(12) United States Patent
Shonteff

(10) Patent No.: US 10,182,811 B2
(45) Date of Patent: Jan. 22, 2019

(54) MICRO SEWING DEVICE

(76) Inventor: Harry Shonteff, San Francisco, CA (US)

( * ) Notice: Subject to any disclaimer, the term of this patent is extended or adjusted under 35 U.S.C. 154(b) by 564 days.

(21) Appl. No.: 13/590,190

(22) Filed: Aug. 21, 2012

(65) Prior Publication Data

US 2014/0058413 A1 Feb. 27, 2014

(51) Int. Cl.
*A61B 17/04* (2006.01)

(52) U.S. Cl.
CPC ...... *A61B 17/0491* (2013.01); *A61B 17/0469* (2013.01)

(58) Field of Classification Search
CPC ...... A61B 17/0057; A61B 2017/00646; A61B 2017/00663; A61B 2017/00654; A61B 2017/0065; A61B 17/0469; A61B 17/0482; A61B 17/06004; A61B 2017/06042; A61B 17/00491; A61B 2017/00495
See application file for complete search history.

(56) References Cited

U.S. PATENT DOCUMENTS

| | | | | |
|---|---|---|---|---|
| 5,613,974 A * | 3/1997 | Andreas et al. | ............ | 606/144 |
| 5,728,114 A * | 3/1998 | Evans et al. | ............ | 606/148 |
| 6,896,692 B2 * | 5/2005 | Ginn et al. | ............ | 606/213 |
| 7,235,087 B2 * | 6/2007 | Modesitt et al. | ............ | 606/144 |
| 8,333,787 B2 * | 12/2012 | Pipenhagen et al. | ............ | 606/213 |
| 2008/0215088 A1 * | 9/2008 | Hnojewyj et al. | ............ | 606/214 |
| 2009/0223426 A1 * | 9/2009 | Shonteff et al. | ............ | 112/169 |
| 2010/0042118 A1 * | 2/2010 | Garrison et al. | ............ | 606/148 |
| 2013/0190808 A1 * | 7/2013 | Tegels et al. | ............ | 606/213 |
| 2013/0190812 A1 * | 7/2013 | Vidlund | ............ | 606/214 |
| 2013/0190813 A1 * | 7/2013 | Tegels et al. | ............ | 606/214 |

* cited by examiner

*Primary Examiner* — Wade Miles
(74) *Attorney, Agent, or Firm* — Walt Froloff

(57) ABSTRACT

The present invention relates to micro-sewing devices, specifically a micro-sewing device for percutaneous, endoscopic, laparoscopic and minimally invasive surgical procedures for suturing in small areas. The device allows for sewing-off and stitching in either direction, in very tight spaces.

13 Claims, 6 Drawing Sheets

MICRO SEWING DEVICE

FIELD OF THE INVENTION

The present invention generally relates to sewing devices and more specifically, to very small sewing devices for micro dimension precision needed in surgical environments.

BACKGROUND

Precision stitching in the last several decades has grown more widely in the medical industry because simply, surgeons sew where they can to remove abnormalities or install continuing smaller medical devices. It is a skill honed and mastered early, used virtually in every procedure they are called upon to perform. Originating from basic fabric sewing, it is not that difficult and with practice relatively safe. However, the trend in surgery of implanting medical devices organ removal and bypass type surgical procedures has grown while device size has shrunk.

Some medical device manufacturing companies are now offering suturing systems and devices aimed at delivering the tactile control and precision associated with open procedures to minimally invasive surgery.

Present surgical procedures are challenged for device placement in difficult if not thought to be impossible locations previously and much smaller suturing work spaces. As medical devices grow smaller, components must become stronger to handle the resulting stresses, and surgical techniques and tools must change to meet the challenge of working with yet smaller devices with smaller working spaces. This applies to endoscopic, laparoscopic and minimally invasive surgical procedures as well as more traditional medical procedures.

Some procedures for device implantation have proven inadequate because of weakened attachment and dislodged devices pose ongoing danger. The securing of many medical devices such as stints requires suturing into tissue and onto new and tougher artificial materials, weaves and fabrics. The securing of these potentially dislodged devices is problematic, requiring smaller sewing devices and stronger needles. Smaller devices generally mean weaker needles, and any breakages from weakened sutures or overstressed needles adds to the operation risk. But smaller devices also means less intrusive means of suturing, simplifying the healing, and speeding recovery.

Where the risk is too high, a particular otherwise helpful medical procedure cannot be used. What is needed is: smaller stitching devices, devices which can suture a running stitch or continuous chain of stitching without tearing the tissue or the compromising the thread. What are needed are stitching devices which give the surgeon more precise thread control.

Very Small Tubular Devices

Catheters and other medical devices require very small tubular shapes to enable deployment in the arteries. Many products like Endovascular stent grafts for abdominal and thoracic aortic aneurysms are made of tubular shaped graft material that is ether hand sewn together or precision sewn by machine like the small arm lock stitch machine as taught by Sew Fine™, in 2002 or on sewing devices like the Endovascular deployment machines used to sew deployment sheaths as taught by Sew Fine™, in 1997 and additional equipment provided in 2006. Medical devices used in procedures to support blood vessels, such as Endovascular stent graft, and devices to keep a vessel open, as in coronary stints, it is often the case that the devices are smaller then can be sewn mechanically because the precision cannot meet the dimensional requirements of the work.

The evolving requirements of medical devices and other non-medical devices press the envelope for sewing on smaller parts and yet smaller parts. In attaching endovascular devices, it is often the case that a sewn device requires a smaller more protective stitching needle then what is currently available. Heart tissue weaknesses can be strengthened with suture repairs. Also, with new technologies evolving in the coronary and other endovascular devices, it is necessary to sew closer to a stent or device than is currently possible. What is needed are smaller stitching devices, small enough to work around stent devices, yet strong enough not to break during the procedure and with thread strong enough to last after the procedure has been completed.

What is needed are percutaneous surgeries that can be performed in such a manner as to limit the amount of recovery time required, and leave no visible scars.

One such surgery is called transgastric surgery, or natural orifice translumenal endosurgery, and involves passing flexible surgical tools and a camera in through the patient's mouth to reach the abdominal cavity via an incision made in the stomach lining. Once the operation is over, the surgeon draws any removed tissue out through the patient's mouth and stitches up the hole in the stomach. Surgeons have performed appendectomies through the mouth.

In many ways, transgastric surgery is a natural extension of keyhole surgery, in which slim surgical tools are inserted into the abdomen via small incisions in the skin, avoiding a large cut in the belly. It has now become routine for procedures such as gall bladder removal.

Transgastric surgery promises to go one better. Much of the discomfort and recovery time after conventional surgery, even keyhole surgery, is due to the incisions made in the abdominal wall. However, because transgastric surgeons reach the abdominal cavity through the mouth, there is no need for an incision, so patients should be back up on their feet much faster. Although an incision is still made in the stomach lining, this is relatively painless, because the stomach has fewer nerve fibers that register pain than our skin. The reduced pain also makes it possible for the procedure to be carried without. Consequently, elderly or infirm patients who may otherwise not be fit enough to receive a general anesthetic, could be treated in this manner.

Going in via the esophagus to the stomach may also reduce the risk of post-operative infections with, say, the drug-resistant superbug MRSA, which often lives on the skin. If you don't have skin incisions then you don't get MRSA. And while there is a risk of infecting the abdominal cavity with bacteria from the gastrointestinal tract, animal studies suggest that risk is small because stomach acid is cleansing.

What is needed is surgery that can be made pain-free, convalescence-free and scar-free, whilst reducing the risk of complications and infections.

Stapling is used to close opened tissue in some procedures. However, staples instead of sutures provide a large form body for the body to attack. Also stapling is not a flexible connector often altering the original, natural attachment and the scar tissue is generally more prevalent as a result of stapling. Also, with suture you have the options of using different types, sizes, and strength of suture. What is needed are more suture options. Thus, what is needed are micro sized suturing devices and procedures which can be used in endoscopic, laparoscopic and minimally invasive surgical procedures.

Common Catheterization Procedures

The most common types of interventional catheterization procedures are those performed to: create septal defects, open stenotic valves, open stenotic vessels, close abnormal vessels, or close certain septal defects. Devices and procedures to do these kinds operations are needed, more efficiently and effectively, with less recovery time, smaller chances of infection, and all around cleaner.

Atrial septal defect (ASD) is a hole in the wall, septum, between the heart's two uppermost chambers, the right and left atrium. This hole allows blood to flow in either direction between the left and right atrium. ASDs may cause several problems. First, this creates a condition in which the right side of the heart now contains extra blood, and extra blood also now flows to the lungs. This diversion of blood puts strain on the heart because it has to pump this extra blood to the lungs. In addition, the strain put on the right-sided pumping chamber can lead to a weakening or enlargement of the right side of the heart and eventually heart failure, if left untreated. This enlargement may also cause arrhythmias (irregular heart rhythms) to develop. This extra blood flow to the lungs may damage the arteries to the lungs over time, leading to high blood pressure in these vessels. Also, ASDs in some circumstances can allow blood clots from the body to enter the brain and cause a stroke. Open heart surgery is currently the only option and is done only after all other solutions have failed. What is needed is a small device or procedure to close the hole invasively, so that more drastic, possibly catastrophic, and expensive solutions are not the only option.

SUMMARY

The present invention discloses a micro-sewing device having a rotary stitch mandrel oriented at 90 degrees to a needle. A suture retainer timed to move with the rotary stitch mandrel, so that the mandrel suture is held behind the needle. The mandrel suture forms a triangle through which the needle and needle suture pass. Thus, forming a stitch.

Another embodiment of the invention includes a suture cast off. The suture cast off aids in stitch formation by removing the suture from the rotary stitch mandrel.

In an alternate embodiment, the invention includes a suture slide control. The suture slide control adjusts tension on the mandrel suture.

DETAILED DESCRIPTION

Figure 1:
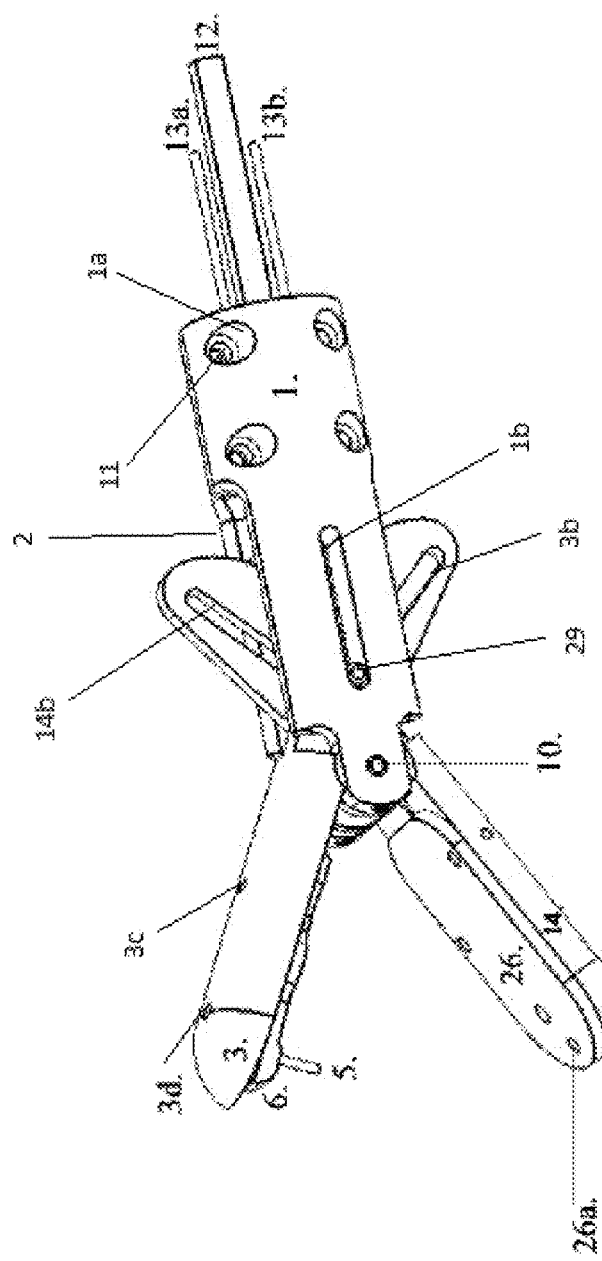
FIG. 1 is a perspective view of a micro sewing device according to an embodiment of the present invention.

In the preferred embodiment displayed in FIG. 1, Left housing 1 and right housing 2 are secured by housing mount screws 11 passing through housing mount screw holes 1a.

The housings 1, 2 secure the sewing head to door driver 12 by means of door driver pin 29. Left housing 1 and right housing 2 each have a pin mount slot 1b that allows for the longitudinal motion of door driver pin 29, when door driver 12 is actuated. Housings 1, 2 have relief cuts that allow top door 3 and lower door 4 to pass through when actuated by door driver 12. Housings 1, 2 contain holes to mount door hinge pin 10.

Figure 2:
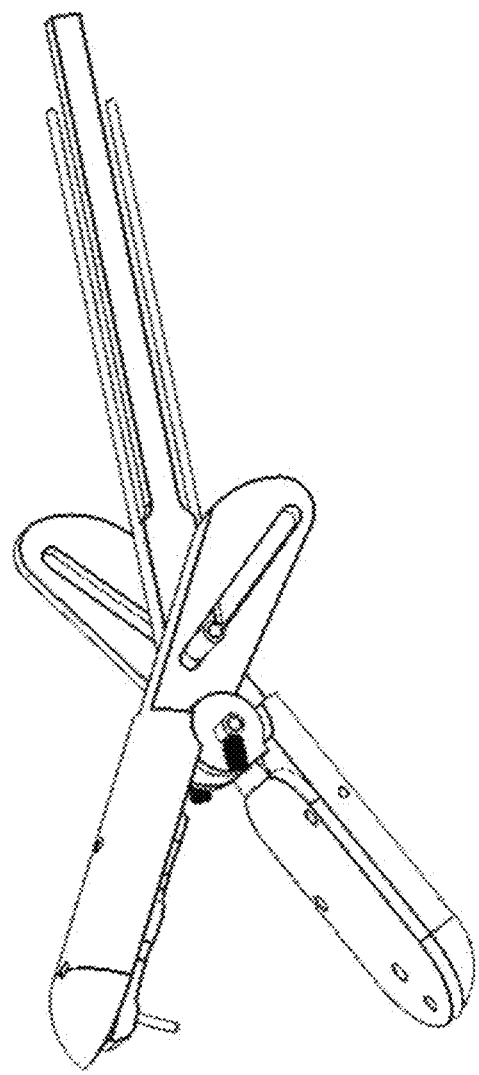
FIG. 2 is a perspective view of the micro sewing device with the housing removed.

As shown in FIGS. 1 and 2, door hinge pin 10 passes through holes in top door 3 and lower door 14, allowing rotational motion around door hinge pin 10 when door driver 12 is actuated. Top door 3 includes top cam track 3b. Lower door 14 includes lower cam track 14b. Door driver pin 29 passes through top cam track 3b, door driver 12, and lower cam track 14b.

The top door assembly will be described with reference to FIGS. 1 and 3. Needle 5 is secured to needle holder 4. Needle 5 may be retained against needle holder 4 by pressure from a screw passing through needle holder 4. Alternatively, needle 5 may be affixed with a threaded portion or permanently attached by welding or other means. Needle holder 4 is retained by a screw (not shown) that passes through hole 3d in top door 3, needle holder 4 and into needle mount 4c. Needle holder 4 is attached to top door 3 by an additional screw (not shown) that passes through holes 4a.

Needle 5 passes through needle slot 6b of foot 6. Foot 6 is pivotally attached to needle holder 4 by foot mount pin 7. Spring 8 (not shown) resides between foot 6 and needle holder 4 in spring mount 6c.

The lower door assembly will be described with reference to FIGS. 1, 3, and 4. Mandrel cover 26 is secured to lower door 14 by screws (not shown) that pass through mandrel cover 26 and lower door 14. Mandrel cover 26 includes needle slot 26a that allows needle 5 to pass through mandrel cover 26 and interface with rotary stitch mandrel 15. Mandrel tensioner 20 is secured between a pin attached to rotary stitch mandrel 15 and pin 14f that is secured to lower door 14. Mandrel tensioner 20 may be a spring, rubber band or other means of exerting force on rotary stitch mandrel 15. Suture retainer tensioner 22 is secured to suture retainer 21 and pin 14g that is secured to lower door 14.

Rotary stitch mandrel 15 is rotationally attached to pin 14e that is secured to lower door 14. Cable 30 is attached to rotary stitch mandrel 15 and resides in track 15b. Cable 30 passes through housing 1, 2 and outside the body, parallel to door driver 12. Suture retainer 21 is rotationally attached to pin 14h that is secured to lower door 14. The motion of suture retainer 21 is limited based on its geometry and its interaction to the pin attached to rotary stitch mandrel 15. Left suture slide control 17 and right suture cast off 18 are mounted to lower door 14 by screws 19 and 19a.

Needle suture tube 13a and lower suture tube 13b pass roughly parallel to door driver 12. Needle suture 24 passes through needle suture tube 13a and through needle 5. Lower suture 31 passes through lower suture tube 13b and through rotary stitch mandrel 15. Sutures 24 and 31 exit outside the body, allowing control of tension on the sutures.

In use, tension of foot spring 8 separates foot 6 from needle holder 4. door driver 12 is actuated causing door driver pin 29 to move laterally. As door driver pin 29 moves away from door hinge pin 10, top door 3 and lower door 14 are moved together. The material to be sewn (tissue) is captured between foot 6 and mandrel cover 26. This causes clamping and compression of the tissue prior to entry of needle 5. As a result, there is a reduced thickness of material for needle 5 to pass through. Further, the additional stability of the material results in needle 5 being subjected to less side pressure, reducing the likelihood of breakage. Additionally, the force from foot spring 8 maintains pressure between foot 6 and mandrel cover 26, while needle 5 is withdrawn.

After needle 5 passes through the material, it passes through needle slot 26a in mandrel cover 26. As it passes below mandrel cover 26, needle 5 interfaces with rotary stitch mandrel 15 causing a stitch to begin. Stitch formation is discussed in detail later in the description.

As door driver pin 29 moves toward door hinge pin 10, top door 3 and lower door 14 are moved apart. Needle 5 is removed from the material while the force from foot spring 8 maintains pressure on the material between foot 6 and mandrel cover 26. The pressure also aids in forcing needle 5 from the material, preventing needle 5 from getting stuck in the material.

FIG. 7 describes stitch formation details. 1. The needle 5 is on the up stroke and forms a loop in the needle suture 24. The rotary stitch mandrel 15 advances through the needle loop. 2. The needle 5 is on the up stroke and rotary stitch mandrel 15 advances through the needle suture 24. 3. The needle 5 is at TDP (top dead center) and is ready to be advanced to the next stitch location. 4. The needle 5 is on the down stroke. The needle 5 enters the thread triangle formed by the lower suture 31 being held in the correct spot. 5. Needle 5 is on the down stroke. Needle suture 24 is east off the rotary stitch mandrel 15. 6. Needle 5 is on the up stroke. Needle suture 24 forms a loop and the rotary stitch mandrel 15 goes through the loop. 7. Needle 5 in on the up stroke. When the needle 5 gets to top dead center the machine can be moved to the next stitch location.

Figure 3:
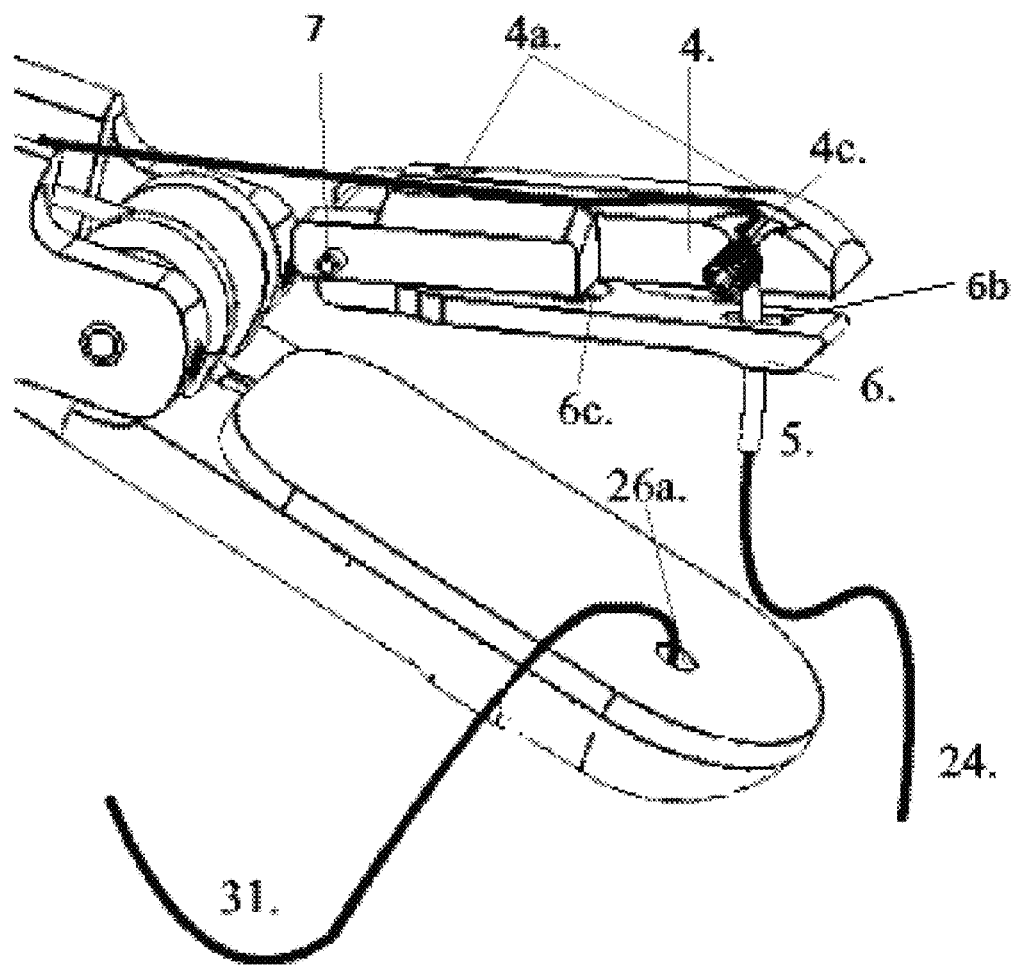
FIG. 3 is a cut-away perspective view of the interior of the top door assembly of the micro sewing device.
Figure 4:
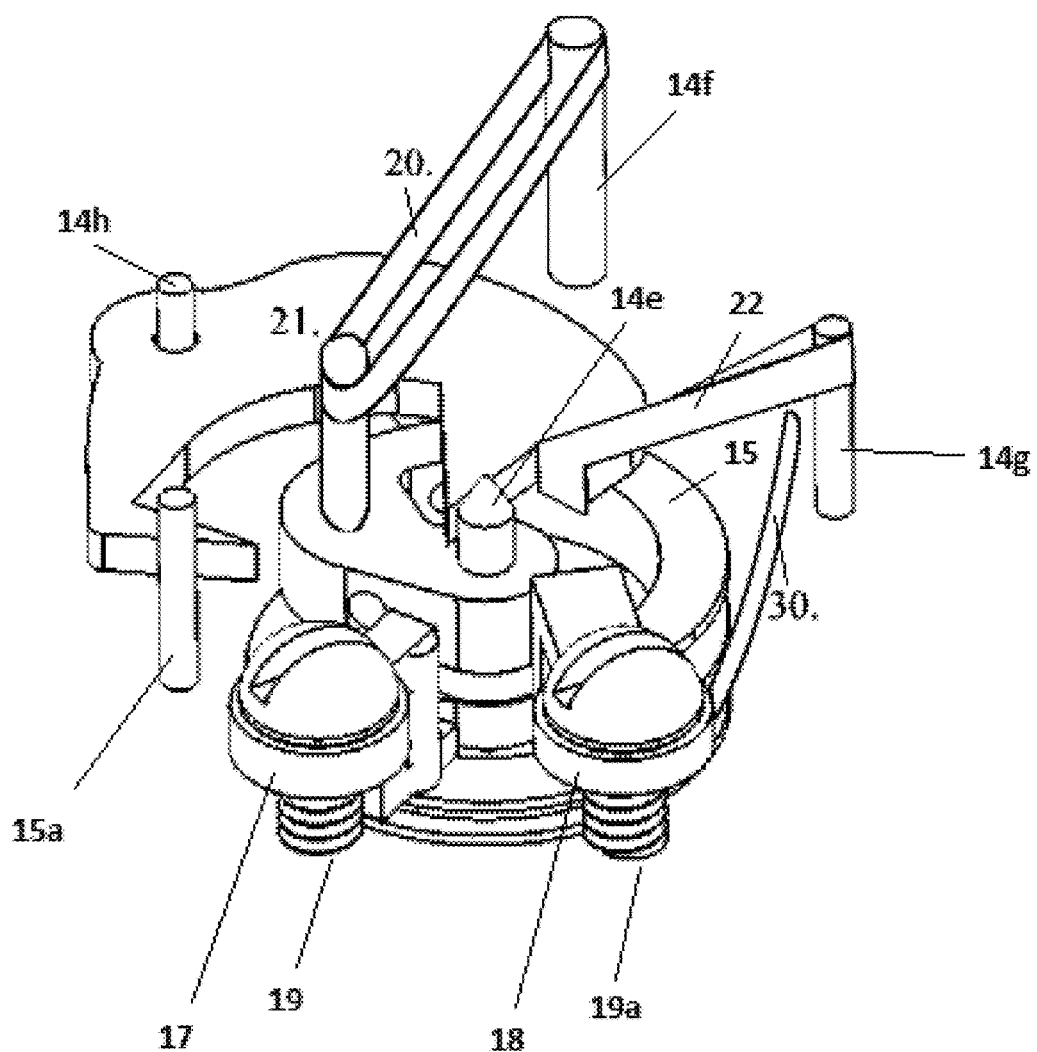
FIG. 4 is a perspective view of the rotary stitch mandrel and suture retainer.
Figure 5:
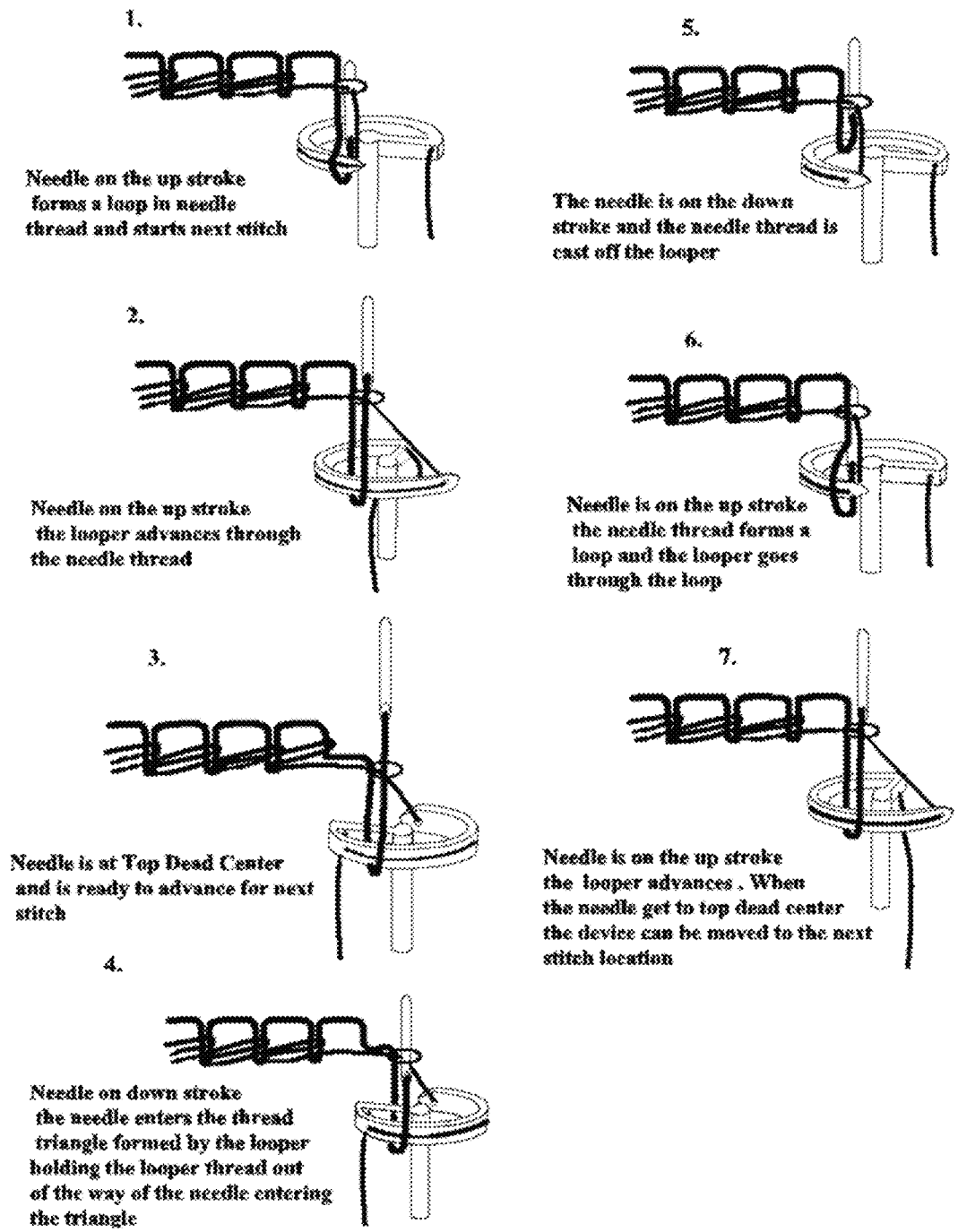
FIG. 5 is a series of images showing the movement of the rotary stitch mandrel and the needle, as a stitch is formed.
Figure 6:
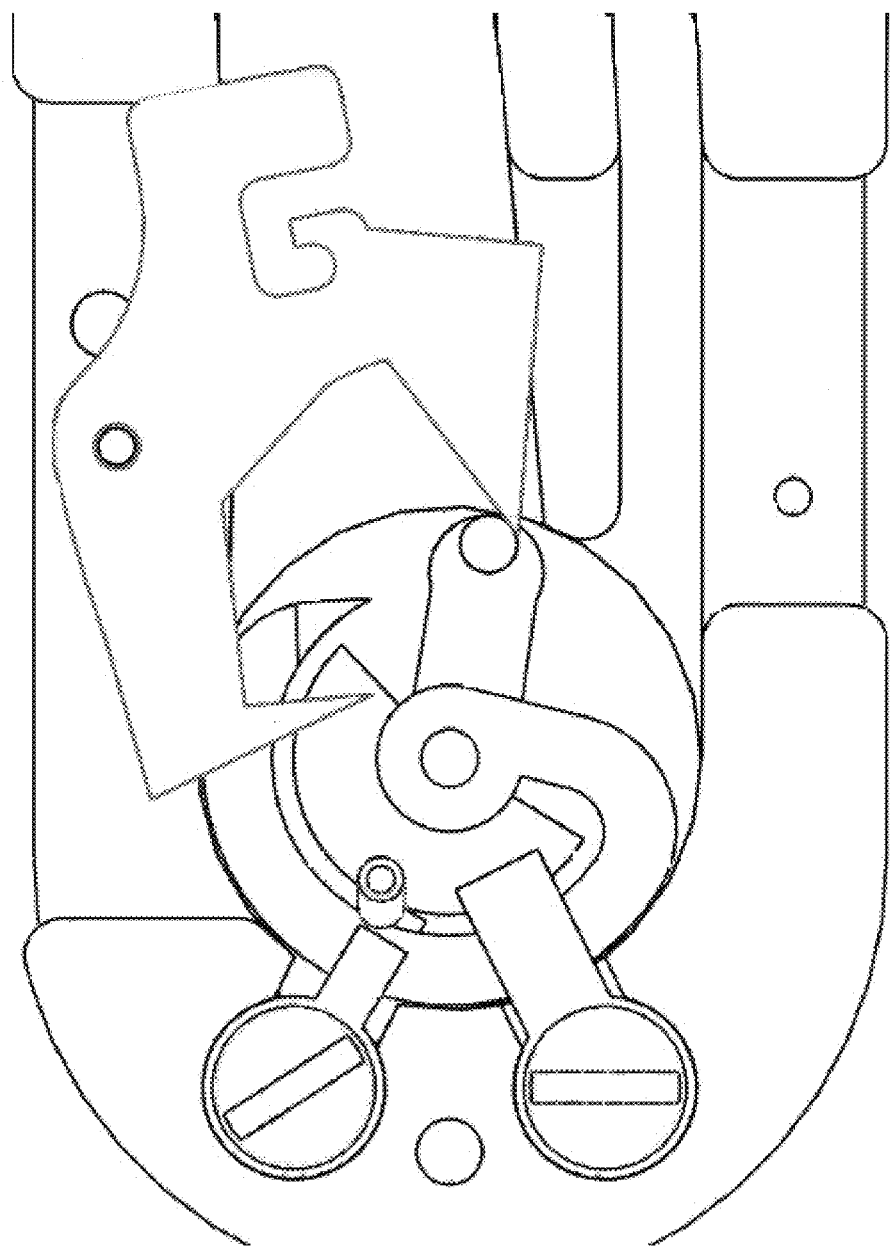
FIG. 6 is a top view, with the mandrel cover removed, showing the motion of the suture retainer with respect to the rotary stitch mandrel; located in the lower door.

From FIGS. 3 and 4, rotary stitch mandrel 15 is moved by cable 30. Cable 30 may be actuated externally by a surgical handle or by electronic means, as taught by Intuitive surgical (divenchi machine). Alternatively, cable 30 may be actuated by means of a pulley or other attachment to either door 3, 14; resulting in movement of cable 30 (and therefore, rotary stitch mandrel 15) as doors 3, 14 are actuated. Movement of rotary stitch mandrel 15 is timed to coincide with the motion of needle 5, as described in the suture formation steps above.

Suture retainer 21 is timed to move with rotary stitch mandrel 15. In the exemplary embodiment, timing is achieved by the curved shape of suture retainer 21 being driven by a pin attached to rotary stitch mandrel 15. The timing results in suture retainer 21 coming into contact with lower suture 31. Lower suture 31 is held behind needle 5 on the down stroke described previously. This results in a consistent suture triangle, allowing needle 5 and upper suture 24 to pass through the triangle. After needle 5 passes through the suture triangle, suture retainer 21 moves and releases lower suture 31. Lower suture 31 forms a loop around needle 5. As needle 5 moves on the upstroke, the loop is drawn tight into a completed suture.

This suture retainer 21 consistently controls the position of lower suture 31 behind needle 5, on the down stroke. This allows for consistent formation of completed sutures regardless of the direction a new suture takes from a previous suture. e.g. a new suture can be formed to the left or right of a previous suture.

Left suture slide control 17 controls the feed of lower suture 31 as it passes into and around rotary stitch mandrel 15. As rotary stitch mandrel 15 arrives at the cast of position described above, lower suture 31 encounters right suture cast off 18. As rotary mandrel 15 passes right suture cast off 18, lower suture 31 is removed from rotary mandrel 15. Right suture cast off 18 Mandrel tension 20 returns rotary stitch mandrel 15 to an at rest position as the tension from cable 30 is released.

Left suture slide control 17 functions to keep needle suture 24 from traveling when it is in contact with rotary stitch mandrel 15. Additionally, when rotary stitch mandrel 15 is at the opposite end of its stroke, right suture cast off 18 assists in pushing needle suture 24 off of rotary stitch mandrel 15 and completing a stitch.

As needle 5 descends through the mandrel cover slot 26a, lower suture 31 must be held in a specific position to allow for sewing in all directions. Suture retainer 21 holds lower suture 31 in position for descending needle 5 to start a stitch. Suture retainer tensioner 22 returns suture retainer 21 to an at rest position. As the rotary stitch mandrel 15 moves, it moves suture retainer 21 in a timed motion to coincide with the loop of needle suture 24 passing from needle 5.

While the stitch created in the preferred embodiment is a 401 2-thread stitch, it is understood that the invention could be modified to create other stitches without departing from its scope and spirit.

Although particular embodiments of the invention have been illustrated and described, various changes may be made in the form, construction and arrangement of the parts herein, without sacrificing any of its advantages. It is understood that all matter herein is to be interpreted as illustrative and not in any limiting sense and it is intended to cover in the appended claims such changes and modifications as come within the spirit and scope of the invention.

What is claimed is:

1. A micro sewing device comprising:
a needle rigidly attached to a top door;
a needle suture associated with the needle;
a rotary stitch mandrel rotationally attached to a lower door and oriented orthogonally to the needle;
a mandrel actuator attached to the rotary stitch mandrel;
a mandrel suture associated with the rotary stitch mandrel;
the top door and the lower door rotationally attached to a main housing;
the main housing coupled to a door driver;
a suture retainer, synchronized with the rotary stitch mandrel;
wherein: a first movement of the door driver causes the top door and the lower door to move together, the needle nearing the rotary stitch mandrel;
a first actuation of the mandrel actuator, in which the rotary stitch mandrel rotates relative to the needle, away from an original position;
the suture retainer moving relative to the rotary stitch mandrel, and holding the mandrel suture behind the needle, forming a loop;
the needle and needle suture passing through the loop and interacting with the mandrel suture to form a stitch;
a second movement of the door driver causes the top door and lower door to separate, drawing the stitch tight automatically;
a second actuation of the mandrel actuator, causing the rotary stitch mandrel to return to the original position.

2. The device of claim 1, further comprising: a mandrel tensioner attached to the rotary stitch mandrel; wherein the second actuation occurs automatically when the mandrel actuator is released, due to the mandrel tensioner.

3. The device of claim 1, further comprising: a mandrel cover attached to the lower door; the mandrel cover having a needle slot;

the mandrel cover covering the rotary stitch mandrel while allowing association between the needle and the rotary stitch mandrel through the needle slot.

4. The device of claim 1, further comprising: a suture slide control associated with the rotary stitch mandrel;
the suture slide control orienting the mandrel suture in position to associate with the needle suture to form the cross stitch.

5. The device of claim 4, further comprising: a suture cast off associated with the rotary stitch mandrel;
the suture cast off removing the cross stitch from the rotary mandrel.

6. The device of claim 1, further comprising: a suture cast off associated with the rotary stitch mandrel;
the suture cast off removing the cross stitch from the rotary mandrel.

7. The device of claim 1, further comprising a door driver pin attached to the door driver;
a lower cam track associated with the lower door; and
a top cam track associated with the top door;
wherein: the first movement and second movement of the door driver cause rotation of the top door and lower door due to movement of the door driver pin riding in the top cam track and lower cam track.

8. A micro sewing device comprising:
a needle rigidly attached to a top door;
a needle suture associated with the needle;
a rotary stitch mandrel rotationally attached to a lower door and oriented orthogonally to the needle;
a mandrel actuator attached to the rotary stitch mandrel;
a mandrel suture associated with the rotary stitch mandrel;
the top door and the lower door rotationally attached to a main housing;
the main housing coupled to a door driver;
a foot located between the top door and the lower door;
a spring applying pressure to the foot, opposite the top door;
a suture retainer, synchronized with the rotary stitch mandrel;
wherein: a first movement of the door driver causes the top door and the lower door to move together, the needle nearing the rotary stitch mandrel;
a first actuation of the mandrel actuator, in which the rotary stitch mandrel rotates relative to the needle, away from an original position;
the suture retainer moving in relation to the rotary stitch mandrel, and holding the mandrel suture behind the needle, forming a loop;
the needle and needle suture passing through the loop and interacting with the mandrel suture to form a stitch;
a second movement of the door driver causes the top door and lower door to separate, drawing the stitch tight automatically;
pressure from the foot preventing stress on the needle and aiding separation of the top door and lower door;
a second actuation of the mandrel actuator, causing the rotary stitch mandrel to return to the original position.

9. The device of claim 8, further comprising: a mandrel tensioner attached to the rotary stitch mandrel; wherein the second actuation occurs automatically when the mandrel actuator is released, due to the mandrel tensioner.

10. The device of claim 9, further comprising: a mandrel cover attached to the lower door; the mandrel cover having a needle slot;
the mandrel cover covering the rotary stitch mandrel while allowing association between the needle and the rotary stitch mandrel through the needle slot.

11. A micro sewing device comprising:
a needle rigidly attached to a top door;
a needle suture associated with the needle;
a rotary stitch mandrel rotationally attached to a lower door and oriented orthogonally to the needle;
a mandrel actuator attached to the rotary stitch mandrel;
a mandrel suture associated with the rotary stitch mandrel;
the top door and the lower door rotationally attached to a main housing;
the main housing coupled to a door driver;
a suture retainer associated with the rotary stitch mandrel;
a suture cast off associated with the rotary stitch mandrel;
wherein: a first movement of the door driver causes the top door and the lower door to move together, causing the needle to associate with the rotary stitch mandrel;
a first actuation of the mandrel actuator, causing the rotary stitch mandrel to rotate relative to the needle, away from an original position;
the suture retainer orienting the mandrel suture in position to associate with the needle suture to form a loop;
the needle passing through the loop, causing the needle suture and the mandrel suture to form a stitch;
a second movement of the door driver, driving the top door and lower door in opposite directions, drawing the stitch tight automatically;
a second actuation of the mandrel actuator, causing the rotary stitch mandrel to return to the original position;
the suture cast off removing the cross stitch from the rotary mandrel.

12. The device of claim 11, further comprising: a mandrel tensioner attached to the rotary stitch mandrel;
wherein the second actuation occurs automatically when the mandrel actuator is released, due to the mandrel tensioner.

13. The device of claim 12, further comprising: a mandrel cover attached to the lower door; the mandrel cover having a needle slot;
the mandrel cover covering the rotary stitch mandrel while allowing association between the needle and the rotary stitch mandrel through the needle slot.

* * * * *